United States Patent
Baxi

(10) Patent No.: US 11,721,435 B2
(45) Date of Patent: Aug. 8, 2023

(54) AUTOMATED QUALITY ASSESSMENT OF PHYSIOLOGICAL SIGNALS

(71) Applicant: Tahoe Research, Ltd., Dublin (IE)

(72) Inventor: Amit S. Baxi, Thane West (IN)

(73) Assignee: Tahoe Research, Ltd., Dublin (IE)

( * ) Notice: Subject to any disclaimer, the term of this patent is extended or adjusted under 35 U.S.C. 154(b) by 673 days.

(21) Appl. No.: 16/418,352

(22) Filed: May 21, 2019

(65) Prior Publication Data

US 2020/0050948 A1 Feb. 13, 2020
US 2020/0210861 A9 Jul. 2, 2020

Related U.S. Application Data

(63) Continuation of application No. 14/780,465, filed as application No. PCT/US2014/041334 on Jun. 6, 2014, now Pat. No. 10,296,835.

(30) Foreign Application Priority Data

Jun. 12, 2013 (IN) .................. IN2556/CHE/2013

(51) Int. Cl.
*G16H 40/63* (2018.01)
*G16H 40/67* (2018.01)
(Continued)

(52) U.S. Cl.
CPC .......... *G16H 40/63* (2018.01); *A61B 5/0022* (2013.01); *A61B 5/486* (2013.01); *A61B 5/6898* (2013.01);
(Continued)

(58) Field of Classification Search
None
See application file for complete search history.

(56) References Cited

U.S. PATENT DOCUMENTS 6,229,856 B1 * 5/2001 Diab .................. A61B 5/14551
375/316
1,211,152 A1 10/2007 Matos
(Continued)

FOREIGN PATENT DOCUMENTS

CN 101504696 8/2009
CN 101848677 9/2010
(Continued)

OTHER PUBLICATIONS

Chinese State Intellectual Patent Office, "Notice on Grant of Patent," issued in connection with Chinese Patent Application No. 201480027219.9, dated Aug. 20, 2019, 4 pages (includes English translation).

(Continued)

*Primary Examiner* — Alan Chen
(74) *Attorney, Agent, or Firm* — Studebaker & Brackett PC

(57) ABSTRACT

Methods and systems may provide for receiving a physiological signal from a sensor configuration associated with a mobile device. A qualitative analysis may be conducted for each of a plurality of noise sources in the physiological signal to obtain a corresponding plurality of qualitative ratings. In addition, at least the plurality of qualitative ratings may be used to determine whether to report the physiological signal to a remote location. In one example, a quantitative analysis is conducted for each of the plurality of noise sources to obtain an overall quality level, wherein the overall quality level is also used to determine whether to report the physiological signal to the remote location.

23 Claims, 5 Drawing Sheets

(51) Int. Cl.
    *A61B 5/00*          (2006.01)
    *G06N 5/04*          (2023.01)
    *G16H 10/60*        (2018.01)

(52) U.S. Cl.
    CPC .......... *A61B 5/7203* (2013.01); *A61B 5/7221* (2013.01); *A61B 5/7475* (2013.01); *G06N 5/04* (2013.01); *G16H 10/60* (2018.01); *G16H 40/67* (2018.01); *A61B 2560/0214* (2013.01)

(56) References Cited

U.S. PATENT DOCUMENTS

| | | |
|---|---|---|
| 7,769,465 B2 | 8/2010 | Matos |
| 7,840,277 B2 | 11/2010 | Matos |
| 8,180,457 B2 | 5/2012 | Matos |
| 8,489,182 B2 | 7/2013 | Duckert et al. |
| 8,805,482 B2 | 8/2014 | Sitzman et al. |
| 10,296,835 B2 | 5/2019 | Baxi |
| 2003/0233129 A1 | 12/2003 | Matos |
| 2007/0043585 A1 | 2/2007 | Matos |
| 2007/0063850 A1 | 3/2007 | Devaul et al. |
| 2007/0299473 A1 | 12/2007 | Matos |
| 2008/0091089 A1 | 4/2008 | Guillory et al. |
| 2008/0091090 A1 | 4/2008 | Guillory et al. |
| 2008/0146892 A1 | 6/2008 | LeBoeuf et al. |
| 2008/0194925 A1 | 8/2008 | Alsafadi et al. |
| 2009/0048497 A1 | 2/2009 | Keren |
| 2009/0082691 A1 | 3/2009 | Denison et al. |
| 2009/0276013 A1 | 11/2009 | Matos |
| 2010/0022903 A1 | 1/2010 | Sitzman et al. |
| 2010/0249625 A1 | 9/2010 | Lin |
| 2010/0324612 A1 | 12/2010 | Matos |
| 2010/0332173 A1 | 12/2010 | Watson et al. |
| 2011/0098112 A1 | 4/2011 | LeBoeuf et al. |
| 2011/0106627 A1 | 5/2011 | LeBoeuf et al. |
| 2012/0108989 A1 | 5/2012 | Gargiulo et al. |
| 2012/0149996 A1 | 6/2012 | Stivoric et al. |
| 2012/0197737 A1 | 8/2012 | LeBoeuf et al. |
| 2012/0203081 A1 | 8/2012 | LeBoeuf et al. |
| 2012/0226111 A1 | 9/2012 | LeBoeuf et al. |
| 2012/0226112 A1 | 9/2012 | LeBoeuf et al. |
| 2013/0096450 A1 | 4/2013 | Duckert et al. |
| 2013/0116580 A1 | 5/2013 | Liu et al. |
| 2013/0278430 A1* | 10/2013 | Poeze ................ A61B 5/14551 340/635 |
| 2014/0107493 A1 | 4/2014 | Yuen et al. |
| 2014/0257058 A1 | 9/2014 | Clarysse et al. |
| 2014/0275855 A1 | 9/2014 | LeBoeuf et al. |
| 2014/0287833 A1 | 9/2014 | LeBoeuf et al. |
| 2014/0288396 A1 | 9/2014 | LeBoeuf et al. |
| 2014/0378787 A1 | 12/2014 | Brumback et al. |
| 2015/0141772 A1 | 5/2015 | LeBoeuf et al. |
| 2015/0335288 A1 | 11/2015 | Toth et al. |
| 2016/0055415 A1 | 2/2016 | Baxi |
| 2016/0317049 A1 | 11/2016 | LeBoeuf et al. |
| 2017/0135636 A1 | 5/2017 | Park et al. |
| 2017/0359635 A1 | 12/2017 | Aumer et al. |
| 2017/0367575 A1 | 12/2017 | Lin |
| 2018/0242859 A1 | 8/2018 | LeBoeuf et al. |
| 2018/0242860 A1 | 8/2018 | LeBoeuf et al. |

FOREIGN PATENT DOCUMENTS

| | | |
|---|---|---|
| CN | 101980228 | 2/2011 |
| CN | 102270264 | 12/2011 |
| JP | 2008-168073 | 7/2008 |
| JP | 2008543127 | 11/2008 |
| JP | 2010029656 | 2/2010 |
| TW | 201112179 | 4/2011 |
| TW | 201134252 | 10/2011 |
| TW | I353242 | 12/2011 |
| WO | 2010111651 | 9/2010 |
| WO | 2013066642 | 5/2013 |

OTHER PUBLICATIONS

Chinese State Intellectual Patent Office, "First Office Action," issued in connection with Chinese Application No. 201480027219.9, dated Jun. 1, 2018, 8 pages.

European Patent Office, "Summons to attend oral proceedings pursuant to Rule 115(1) EPC," issued in connection with European Patent Application No. 14811376.4, dated Jul. 24, 2019, 9 pages.

Laciar et al. "An Improved Weighted Signal Averaging Method for High-Resolution ECG Signals," Computers in Cardiology, 2001, vol. 28, pp. 69-72, 4 pages.

Blanco-Velasco et al., "ECG signal Denoising and Baseline Wander Correction Based on the Empirical Mode Decompostion," Computers in Biology and Medicine, 2008, vol. 38, pp. 1-13, 13 pages.

Korean Intellectual Property Office, "Notice of Allowance," issued in connection with Korean Patent Application No. 20157032275, dated Oct. 20, 2017, 3 pages. (English translation provided).

European Patent Office, "Communication pursuant to Article 94(3) EPC," issued in connection with European Patent Application No. 14811376.4, dated Jul. 24, 2018, 6 pages.

Taiwanese Patent Office, "Notice of Allowance," issued in connection with Taiwanese Patent Application No. 103118238, dated Oct. 30, 2015, 2 pages.

Japenese Patent Office, "Decision to Grant," issued in connection with Japanese Patent Application No. 2016-514172, dated Apr. 11, 2017, 3 pages.

Chinese State Intellectual Patent Office, "Second Office Action," issued in connection with Chinese Patent Application No. 201480027219.9, dated Feb. 20, 2019, 6 pages.

Korean Intellectual Property Office, "Notice of Final Rejection," issued in connection with Korean Patent Application No. 20157032275, dated Aug. 21, 2017, 6 pages (includes English translation).

Indian Patent Office, "Notice of Grant," issued in connection with Indian Patent Application No. 2556/CHE/2013, dated Sep. 10, 2019, 2 pages.

International Searching Authority, "International Search Report and Written Opinion," issued in connection with International Patent Application No. PCT/US2014/041334, dated Oct. 2, 2014, 8 pages.

International Bureau, "International Preliminary Report on Patentability," issued in connection with International Patent Application No. PCT/US2014/041334, dated Dec. 15, 2015, 6 pages.

India Patent Office, Office Action for Indian Patent Application No. 2556/CHE/2013, dated Oct. 26, 2018, 5 pages. (Document not provided. Copy provided in parent U.S. Appl. No. 14/780,465).

Taiwanese Patent Office, Office Action and Search Report for Taiwanese Patent Application No. 103118238, dated Jul. 6, 2015, 30 pages Including 15 pages of English translation. (Document not provided. Copy provided in parent U.S. Appl. No. 14/780,465).

Korean Patent Office, Office Action for Korean Patent Application No. 2015-7032275, dated Feb. 7, 2017, 13 pages including 6 pages of English translation. (Document not provided. Copy provided in parent U.S. Appl. No. 14/780,465).

European Patent Office, European Search Report for European Patent Application No. 14780465-4, dated Jan. 23, 2017, 7 pages. (Document not provided. Copy provided in parent U.S. Appl. No. 14/780,465).

Japanese Patent Office, Office Action for Japanese Patent Application No. 2016-514172, dated Nov. 29, 2016, 6 pages including 3 pages of English Translation. (Document not provided. Copy provided in parent U.S. Appl. No. 14/780,465).

United States Patent and Trademark Office, "Non-Final Office Action," issued in connection with U.S. Appl. No. 14/780,465, dated Jul. 12, 2018, 8 pages. (Document not provided. Copy available in parent U.S. Appl. No. 14/780,465).

United States Patent and Trademark Office, "Notice of Allowance," issued in connection with U.S. Appl. No. 14/780,465, dated Jan. 9, 2019, 5 pages. (Document not provided. Copy available in parent U.S. Appl. No. 14/780,465).

European Patent Office, "Extended European Search Report," issued in connection with European Patent Application No. 20153449.2, dated Mar. 31, 2020, 9 pages.

(56) References Cited

OTHER PUBLICATIONS

Leski et al., "ECG Baseline Wander and Powerline Interface Reduction Using Nonlinear Filter Bank," Signal Processing, 2005, vol. 85, pp. 781-793, 13 pages.

European Patent Office, "Decision to Refuse European Patent Application," issued in connection with European Patent Application No. 14811376.4, dated Jul. 15, 2020, 20 pages.

European Patent Office, "Communication pursuant to Article 94(3) EPC," issued in connection with European Patent Application 20153449.2, dated Dec. 9, 2021, 6 pages.

* cited by examiner

AUTOMATED QUALITY ASSESSMENT OF PHYSIOLOGICAL SIGNALS

CROSS-REFERENCE TO RELATED APPLICATIONS

This patent arises from a continuation of U.S. patent application Ser. No. 14/780,465, filed Sep. 25, 2015, entitled "AUTOMATED QUALITY ASSESSMENT OF PHYSIOLOGICAL SIGNALS," which is a national stage entry of International Patent Application Serial No. PCT/US2014/041334, filed Jun. 6, 2014, entitled "AUTOMATED QUALITY ASSESSMENT OF PHYSIOLOGICAL SIGNALS." The contents of these applications are hereby incorporated herein by reference in their entireties.

BACKGROUND

Technical Field

Embodiments generally relate to health monitoring. More particularly, embodiments relate to the automated quality assessment of physiological signals in home health monitoring settings.

Discussion

Health monitoring may traditionally involve obtaining physiological signals such as electrocardiogram (ECG) readings from an individual in a clinical setting such as a hospital, doctor's office or other medical center. In such a case, a medical professional may connect various sensors to the individual/patient and interpret the readings in order to make health-related decisions. If the medical professional determines that the ECG readings are not reliable or of adequate quality, the medical professional may make adjustments to the sensing configuration and/or environment prior to making health-related decisions based on those readings. In home use settings, however, patients may often lack the requisite medical and/or technical knowledge to identify unreliable or inferior quality readings and make the appropriate adjustments to the sensing configuration/environment. As a result, suboptimal health care (e.g., improper diagnosis, increased cost and/or increased patient risk) may be experienced.

BRIEF DESCRIPTION OF THE DRAWINGS

The various advantages of the embodiments will become apparent to one skilled in the art by reading the following specification and appended claims, and by referencing the following drawings, in which:

DETAILED DESCRIPTION

Figure 1:
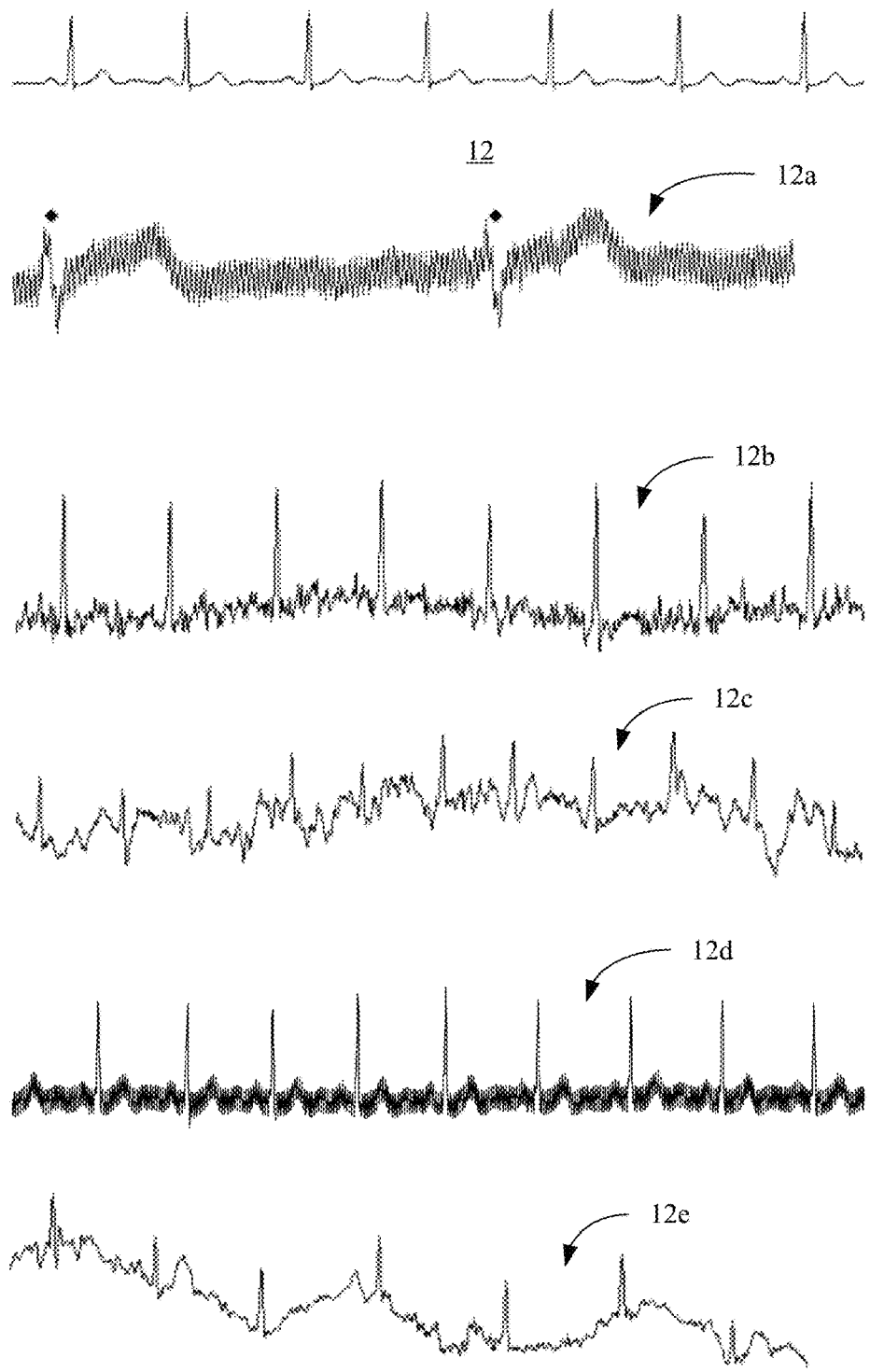
FIG. 1 is an illustration of an example of a set of signals according to an embodiment.

FIG. 1 shows a plurality of signals that may be associated with the monitoring of an individual/patient in a home health setting. In the illustrated example, a physiological signal 10 such as, for example, an electrocardiogram (ECG) signal may be deemed reliable due to a lack of noise in the physiological signal 10. Although the illustrated physiological signal 10 contains ECG information, in other examples, the physiological signal 10 may contain blood pressure information, pulse oximeter information, Electroencephalograph (EEG) information, Photoplethysmograph (PPG) information, and so forth.

Depending upon the sensing configuration and/or environment, a plurality of noise sources 12 (12a-12e) may be superimposed on physiological signals such as the signal 10 and therefore reduce the quality and/or reliability of those signals. For example, a power main (e.g., 50/60 Hz) interference source 12a might originate from nearby low frequency electrical equipment, building power lines, etc. Additionally, a muscle noise source 12b may originate from involuntary muscle contractions of the patient due to anxiety, and a motion artifact noise source 12c may originate from patient movement. Moreover, an electromagnetic interference (EMI) source 12d may originate from nearby high frequency devices such as mobile phones and other electronic devices, and a baseline wander noise source 12e may originate from chemical reactions and other contributors to changes in skin-electrode impedance. Each of the noise sources 12 may therefore have a negative impact on the quality of the measured physiological signal to the extent that the respective type of noise is present in the physiological signal. Indeed, the noise sources 12 may present unique challenges in home health settings due to a relative lack of medical and/or technical knowledge of typical patients.

As will be discussed in greater detail, both a qualitative analysis and a quantitative analysis may be conducted in home health settings for each of the noise sources 12, wherein those analyses may be used to determine whether and when to report the physiological signals to a remote location such as a clinical health setting (e.g., hospital, doctor's office or other medical center). In addition, the analyses may be used to guide patients in modifying the sensor configuration and/or environment in order to increase the reliability of reported physiological signals.

Figure 2A:
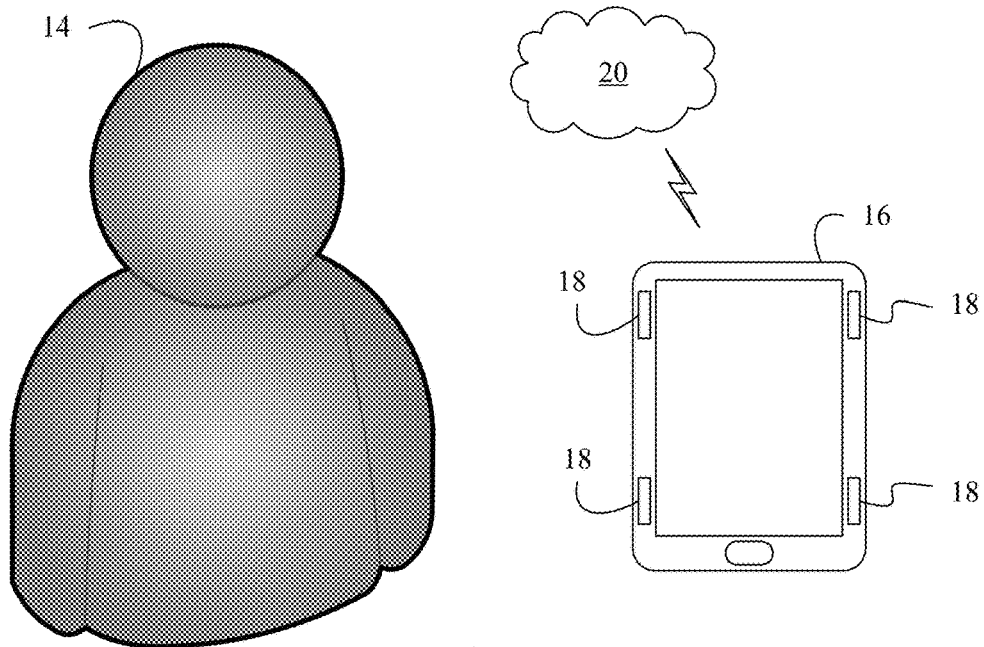
FIGS. 2A and 2B are illustrations of examples of sensing configurations according embodiments.

Turning now to FIG. 2A a home health monitoring environment is shown in which a patient 14 uses a mobile device 16 to take readings such as, for example, ECG readings, blood pressure readings, pulse oximeter readings, EEG readings, PPG readings, and so forth. In the illustrated example, the mobile device 16 includes one or more sensors (e.g., electrodes, contacts) 18 that may be pressed against a body part (e.g., chest, arm, head) of the patient 14 in order to measure the physiological condition of the patient 14. The mobile device 16 may generate one or more physiological signals in conjunction with the readings, wherein the physiological signals may be transmitted to a healthcare network 20. As will be discussed in greater detail, the mobile device 16 may be configured to make automated quality assessments of the physiological signals prior to transmitting them to the healthcare network 20 as well as guide the patient 14 in taking additional readings if the assessments indicate that earlier readings lack reliability.

The healthcare network 20 may in turn provide the reported physiological signals to healthcare professionals such as physicians, nurses, clinicians, and so forth. Additionally, the healthcare professionals may deliver advice to the patient 14 via the healthcare network 20 and/or mobile device 16. In addition to having the integrated sensors 18, the mobile device 16 may be a computing platform such as a wireless smart phone, smart tablet, personal digital assistant (PDA), mobile Internet device (MID), notebook computer, convertible tablet, etc., having other functionality such as messaging (e.g., text messaging, instant messaging/ IM, email), computing, media playing, and so forth.

Figure 2B:
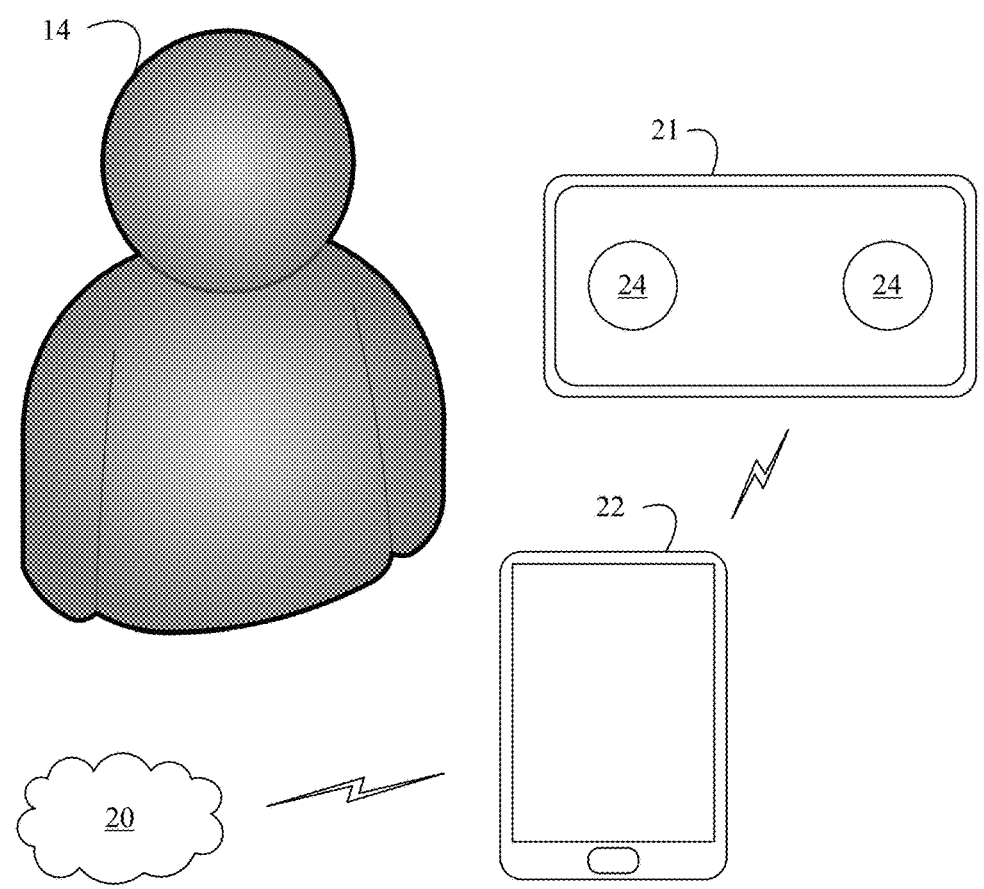

FIG. 2B shows a home health monitoring environment in which the patient 14 uses a measurement accessory 21 and a mobile device 22 to take readings such as, for example, ECG readings, blood pressure readings, pulse oximeter readings, EEG readings, PPG readings, and so forth. In the illustrated example, the measurement accessory 21 includes one or more sensors (e.g., electrodes, contacts) 24 that may be pressed against a body part of the patient 14 in order to measure the physiological condition of the patient 14. The illustrated measurement accessory 21 generates one or more physiological signals in conjunction with the readings, wherein the physiological signals may be transmitted to the mobile device 22. As in the case of the mobile device 16 (FIG. 2A), the measurement accessory 21 or mobile device 22 may be configured to make automated quality assessments of the physiological signals prior to transmitting them to the healthcare network 20 as well as guide the patient 14 in taking additional readings if the assessments indicate that earlier readings lack reliability.

As already discussed, the healthcare network 20 may provide the reported physiological signals to healthcare professionals, who may deliver advice to the patient 14 via the healthcare network 20 and/or mobile device 22. The mobile device 22 may be a computing platform such as a wireless smart phone, smart tablet, PDA, MID, notebook computer, convertible tablet, etc., with messaging, computing, media playing and/or other functionality.

Figure 3:
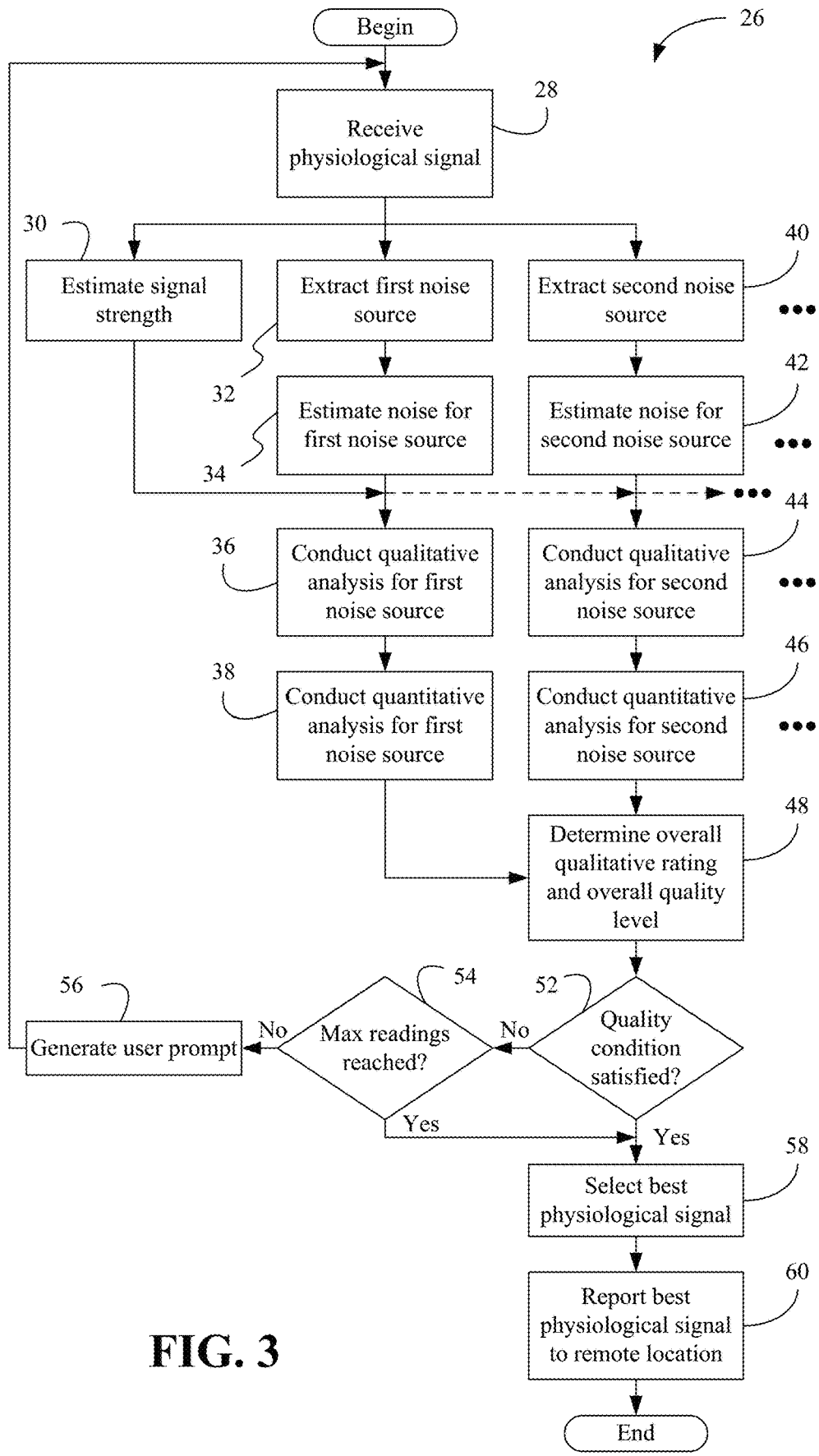
FIG. 3 is a flowchart of an example of a method of evaluating physiological signals according to an embodiment.

FIG. 3 shows a method 26 of evaluating physiological signals in a home health setting. The method 26 may be implemented in executable software as a set of logic instructions stored in a machine- or computer-readable medium of a memory such as random access memory (RAM), read only memory (ROM), programmable ROM (PROM), firmware, flash memory, etc., in configurable logic such as, for example, programmable logic arrays (PLAs), field programmable gate arrays (FPGAs), complex programmable logic devices (CPLDs), in fixed-functionality logic hardware using circuit technology such as, for example, application specific integrated circuit (ASIC), complementary metal oxide semiconductor (CMOS) or transistor-transistor logic (TTL) technology, or any combination thereof. For example, computer program code to carry out operations shown in method 26 may be written in any combination of one or more programming languages, including an object oriented programming language such as Java, Smalltalk, C++ or the like and conventional procedural programming languages, such as the "C" programming language or similar programming languages.

Illustrated processing block 28 provides for receiving a physiological signal from a sensor configuration associated with a mobile device. As already noted, the physiological signal may be associated with an ECG reading, blood pressure reading, pulse oximeter reading, EEG reading, PPG reading, and so forth. The signal strength of the physiological signal may be estimated at block 30. In one example, estimation of the signal strength involves de-noising the physiological signal using multi-band filters. The filters used in the de-noising procedure may take into consideration the frequency profile of various types of noise sources (e.g., power main interference, muscle noise, motion artifact noise, EMI, baseline wander noise). Additionally, block 30 may involve signal processing to identify one or more fiducial points in the filtered signal. For example, a fudicial point in an ECG signal may correspond to an R-wave (i.e., upward deflection in a QRS complex) of the ECG signal. Thus, the fiducial points may be used to calculate the signal strength of the physiological signal.

Block 32 may extract a first noise source from the physiological signal. For example, for the aforementioned baseline wander noise 12e (FIG. 1), block 32 may apply a digital low pass filter (LPF) having a cutoff frequency of 1 Hz, a cubic spline, etc., to the physiological signal. Alternatively, the de-noised physiological signal from block 30 may be subtracted from the signal in block 32 in order to isolate the baseline wander noise 12e from the physiological signal. In this example, the output of block 32 may be only the baseline wander, extracted from the physiological signal. Illustrated block 34 provides for performing noise estimation for the first noise source. For example, for the baseline wander noise 12e (FIG. 1), the noise estimation may involve rejecting outlier data in the isolated baseline wander noise and determining/calculating the area under the resulting curve. The area under the noise curve may be particularly effective for low frequency noise such as baseline wander noise. Block 34 may also provide for normalizing the estimated noise with respect to the physiological signal strength estimated in block 30.

A qualitative analysis may be conducted for the first noise source at block 36. More particularly, an individual qualitative rating—$QR_1$ (e.g., "Good", "Fair", "Poor") may be assigned to the first noise source by comparing the estimated noise for the first noise source to appropriate thresholds. In this regard, since medical professionals typically make visual assessments of physiological signals to decide whether they are of acceptable quality, the qualitative thresholds may be chosen to match manual visual acuity/assessments. For example, the rating criteria might be implemented as given in Table I below.

TABLE I

| Rating Criteria | Individual Qualitative Rating (QR) |
| --- | --- |
| Noise type is not visually apparent in the physiological signal | Good |
| Noise type is present in the physiological signal and is visually apparent in moderate amounts, but the physiological signal may still be visually interpreted for diagnosis | Fair |
| Noise type is present in the physiological signal in excessive amounts such that the physiological signal may not be visually interpreted for diagnosis | Poor |

Illustrated block 38 conducts a quantitative analysis for the first noise source. More particularly, a signal to noise ratio ($SNR_1$) may be computed for the first noise source based on the estimated physiological signal strength from block 30 and the estimated and normalized noise from block 34. As will be discussed in greater detail, the $SNR_1$ for the first noise source may be subsequently combined with the SNRs of the other noise sources to obtain an overall quality level for the physiological signal.

Similarly, block 40 may extract a second noise source from the physiological signal. For example, for the aforementioned power main interference source 12a (FIG. 1), block 40 may apply a digital elliptic band pass filter (BPF) having a center frequency of 50 Hz or 60 Hz, a wavelet transform, etc., to the physiological signal. Alternatively, the de-noised physiological signal from block 30 may be subtracted from the filtered signal in block 40 in order to isolate the power main interference source from the physiological signal. In this example, the output of block 40 may be only the mains 50 or 60 Hz noise, extracted from the physiological signal. Illustrated block 42 provides for performing noise estimation for the second noise source. For example, for the power main interference source 12a (FIG. 1), the noise estimation may involve calculating the peak-to-peak average for the noise curve for the isolated power main interference. The peak-to-peak average may be particularly effective for high frequency noise such as power main interference. Block 42 may also provide for normalizing the estimated noise with respect to the physiological signal strength estimated in block 30.

As in the case of the first noise source, a qualitative analysis may be conducted for the second noise source at block 44. Thus, an individual qualitative rating—QR$_2$ (e.g., "Good", "Fair", "Poor") may be assigned to the second noise source by comparing the estimated noise for the second source to appropriate thresholds, as already discussed with regard to Table I. Illustrated block 46 conducts a quantitative analysis for the second noise source. More particularly, an SNR$_2$ may be computed for the second noise source based on the estimated physiological signal strength from block 30 and the estimated and normalized noise from block 42.

The illustrated noise extraction and estimation procedure may be conducted for each of a plurality of noise sources in the physiological signal. For example, for the muscle noise source 12b (FIG. 1), the noise extraction may involve applying a digital BPF having a center frequency of 2 Hz or 100 Hz to the physiological signal. For the motion artifact noise source 12c (FIG. 1), the noise extraction might involve applying a digital notch filter with a center frequency of 50 Hz or 60 Hz to remove power main interference and applying a digital LPF having a cutoff frequency of 5 Hz, a cubic spline, etc. Noise extraction techniques may be similarly tailored to the EMI source 12d (FIG. 1) and other types of noise in the physiological signal. In each case, the de-noised physiological signal from block 30 may be subtracted from the filtered noise signal in order to isolate the particular type of noise from the physiological signal.

With regard noise estimation, relatively high frequency noise such as the muscle noise source 12b and/or the EMI source 12d may be estimated by calculating the peak-to-peak average for the noise curve. Relatively low frequency noise, on the other hand, such as the motion artifact noise source 12c might be estimated by rejecting outlier data in the isolated noise and determining the area under the resulting curve.

The illustrated qualitative and quantitative analyses may also be conducted for each of the plurality of noise sources. Thus, a plurality of qualitative ratings may be obtained, wherein the plurality of qualitative ratings correspond to the plurality of noise sources. Additionally, a plurality of SNRs may be obtained for the plurality of noise sources. Moreover, after assigning individual qualitative ratings to separate noise types, the individual qualitative ratings (QR$_1$, QR$_2$, . . . ) may be combined using a scoring function to arrive at an overall qualitative rating (OQR) in terms of Good, Fair or Poor. Thus, illustrated block 48 provides for determining an OQR for the physiological signal.

Block 48 may also determine an overall quality level (OQL) for the physiological signal, wherein the OQL may be based on both the individual qualitative analyses (QR$_1$, QR$_2$, . . . ) and the individual quantitative analyses (SNR$_1$, SNR$_2$, . . . ). More particularly, a dynamic weighting function may combine the individual SNRs into a single value (e.g., ranging from zero to ten). The weights in the weighting function may change dynamically if a certain noise type is present in excessive quantity to tilt the physiological signal quality to unacceptable levels. For example, if an ECG signal is contaminated with only baseline wander noise but in amounts to render the ECG signal unreliable, the weighting function may adjust the weight of this particular noise type relative to other noise types so that due consideration is given to a single excessive noise type over mild-to-moderate amounts of multiple noise types that may be acceptable. The dynamic weighting function may be implemented so that OQL is a function of, $$\frac{\sum_{k=1}^{n}(W_k * SNR_k)}{n} \tag{1}$$

Where n is the number of noise types, $W_k$ is a dynamic weight assigned to a particular noise type and $SNR_k$ is the signal to noise ratio of that particular noise type. Thus, in the above expression, the weight $W_k$ of a noise type may dynamically change based upon its corresponding individual qualitative rating ($QR_k$). Block 48 may also provide for storing the de-noised physiological signal as well as the qualitative and quantitative information associated with the physiological signal (e.g., individual QRs, OQR, OQL, etc.) for later use.

Figure 4:
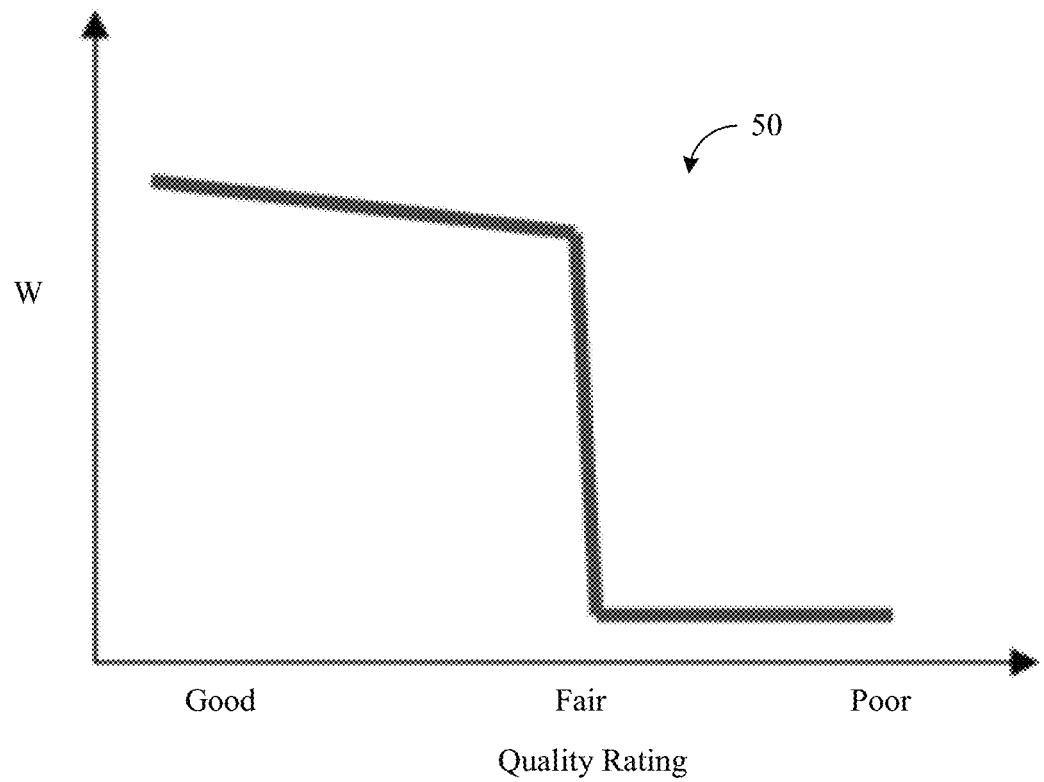
FIG. 4 is a plot of an example of a weighting approach according to an embodiment.

FIG. 4 shows a weighting curve 50 that may be used to assign weights to individual noise types. In general, if the qualitative rating of a particular noise type is Poor, its associated weight may sharply fall toward zero so as to significantly reduce the SNR contribution of that noise type to the OQL. Such an approach may effectively amplify the presence of a noise type in excessive amounts, by significantly reducing the OQL.

Returning now to FIG. 3, a determination may be made at block 52 as to whether a quality condition has been satisfied. The quality condition may specify, for example, that no noise type has an individual QR of "Poor", the OQR is either "Good" or "Fair", the OQL is above a certain threshold (e.g., 5 out of 10), etc., or any combination thereof. If the quality condition is not satisfied, illustrated block 54 determines whether a maximum number of readings (e.g., three) has been reached. If not, a user prompt may be generated at block 56. The user prompt may request one or more additional readings (e.g., "Please take another ECG reading").

The user prompt may also include a recommendation that is tailored to one or more of the plurality of noise sources. For example, in the case of baseline wander noise, the patient might be asked to hold the device lightly and with uniform pressure. In the case of excessive muscle tremor noise, the patient may be asked to relax and support his or her hands. In the case of motion artifact noise, the patient might be asked to remain still or avoid too much chest movement during breathing. In the case of excessive power main interference or EMI, the patient may be asked to change locations and/or power off nearby devices. Other noise type-specific recommendations may also be made. Once the patient has been prompted, the illustrated method 26 may be repeated to obtain a plurality of physiological signals associated with a corresponding plurality of readings, and conduct the qualitative and quantitative analyses for each of the plurality of physiological signals. The resulting physiological signals and associated qualitative and quantitative data may be stored for later use, as already noted.

If either the quality condition is satisfied or the maximum number of readings is reached, block 58 may select the best physiological signal based on the qualitative and quantitative analysis results, wherein the selected best physiological signal (and associated qualitative and quantitative data) is reported to a remote location at illustrated block 60.

Figure 5:
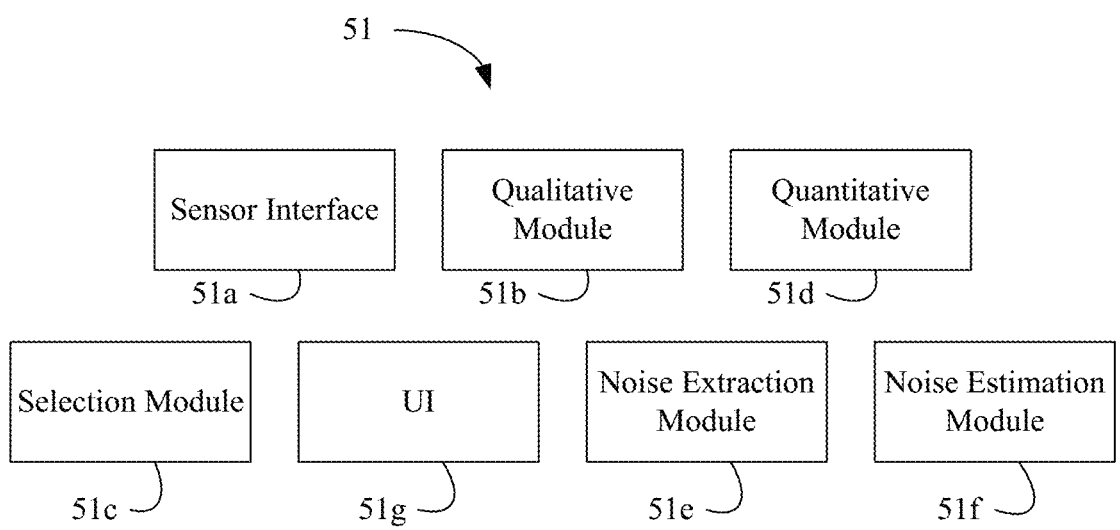
FIG. 5 is a block diagram of an example of a logic architecture according to an embodiment.

FIG. 5 shows a logic architecture 51 (51a-51g) to evaluate physiological signals in a home health setting. In the illustrated example, a sensor interface 51a receives a physiological signal from a sensor configuration associated with a mobile device and a qualitative module 51b conducts a qualitative analysis for each of a plurality of noise sources in the physiological signal to obtain a corresponding plurality of qualitative ratings. A selection module 51c may use at least the plurality of qualitative ratings to determine whether to report the physiological signal to a remote location.

In one example, the architecture 51 also includes a quantitative module 51d to conduct a quantitative analysis for each of the plurality of noise sources to obtain an overall quality level, wherein the overall quality level may also be used to determine whether to report the physiological signal to the remote location. More particularly, the quantitative module 51d may assign weights to signal to noise ratios associated with the plurality of noise sources based on the plurality of qualitative ratings.

Additionally, the qualitative module 51b may combine the plurality of qualitative ratings into an overall qualitative rating, wherein the overall qualitative rating is to be used to determine whether to report the physiological signal to the remote location. The illustrated architecture 51 also includes a noise extraction module 51e to filter, for each of the plurality of noise sources, the physiological signal, and a noise estimation module 51f to conduct a noise estimation for the filtered physiological signal. The architecture 51 may also include a user interface (UI) to generate a user prompt if a quality condition is not satisfied. As already noted, the user prompt may request one or more additional readings and/or include a recommendation that is tailored to one or more of the plurality of noise sources.

Figure 6:
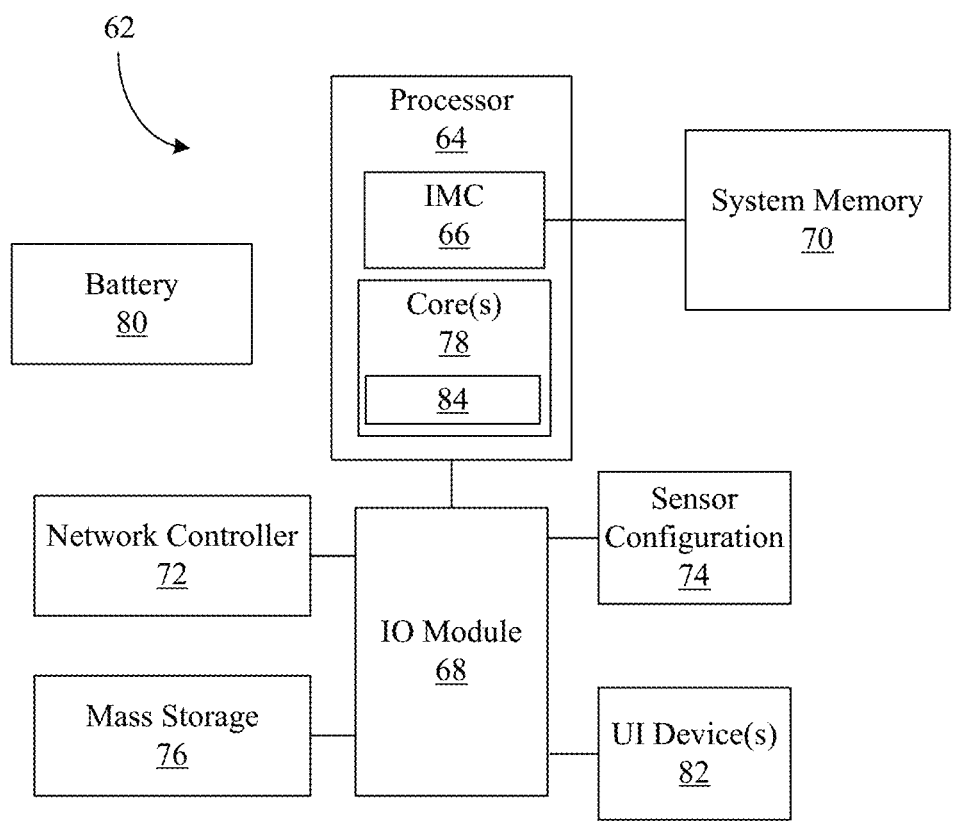
FIG. 6 is a block diagram of an example of a platform according to an embodiment.

Turning now to FIG. 6, a computing platform 62 is shown. The platform 62 may be part of a mobile device having computing functionality (e.g., PDA, laptop, smart tablet), communications functionality (e.g., wireless smart phone), imaging functionality, media playing functionality (e.g., smart television/TV), or any combination thereof (e.g., mobile Internet device/MID). In the illustrated example, the platform 62 includes a processor 64, an integrated memory controller (IMC) 66, an input output (IO) module 68, system memory 70, a network controller 72, a sensor configuration 74, mass storage 76 (e.g., optical disk, hard disk drive/HDD, flash memory), one or more user interface (UI) devices 82 and a battery 80 to supply power to the platform 62. The processor 64 may include a core region with one or several processor cores 78.

The illustrated IO module 68, sometimes referred to as a Southbridge or South Complex of a chipset, functions as a host controller and communicates with the network controller 72, which could provide off-platform communication functionality for a wide variety of purposes such as, for example, cellular telephone (e.g., Wideband Code Division Multiple Access/W-CDMA (Universal Mobile Telecommunications System/UMTS), CDMA2000 (IS-856/IS-2000), etc.), WiFi (Wireless Fidelity, e.g., Institute of Electrical and Electronics Engineers/IEEE 802.11-2007, Wireless Local Area Network/LAN Medium Access Control (MAC) and Physical Layer (PHY) Specifications), 4G LTE (Fourth Generation Long Term Evolution), Bluetooth (e.g., IEEE 802.15.1-2005, Wireless Personal Area Networks), WiMax (e.g., IEEE 802.16-2004, LAN/MAN Broadband Wireless LANS), Global Positioning System (GPS), spread spectrum (e.g., 900 MHz), and other radio frequency (RF) telephony purposes. The IO module 68 may also include one or more wireless hardware circuit blocks to support such functionality. Although the processor 64 and IO module 68 are illustrated as separate blocks, the processor 64 and IO module 68 may be implemented as a system on chip (SoC) on the same semiconductor die.

The system memory 70 may include, for example, double data rate (DDR) synchronous dynamic random access memory (SDRAM, e.g., DDR3 SDRAM JEDEC Standard JESD79-3C, April 2008) modules. The modules of the system memory 70 may be incorporated into a single inline memory module (SIMM), dual inline memory module (DIMM), small outline DIMM (SODIMM), and so forth.

The illustrated cores 78 execute logic 84 to evaluate physiological signals in home health settings as already described with respect to FIGS. 4 and 5. Thus, the logic 84 may receive physiological signals from the sensor configuration 74, conduct a qualitative analysis for each of a plurality of noise sources in the physiological signals to obtain a corresponding plurality of qualitative ratings, and use at least the plurality of qualitative ratings to determine whether to report the physiological signals to a remote location. The logic 84 may also conduct a quantitative analysis for each of the plurality of noise sources to obtain an overall quality level, wherein the overall quality level is also used to determine whether to report the physiological signals to the remote location. User prompts for additional readings may be presented to the patient via the UI devices 82, which may include a display, speaker, and so forth.

Additional Notes and Examples

Example 1 may include a mobile device to evaluate physiological signals, comprising a battery to provide power to the mobile device, a sensor configuration and a sensor interface to receive a physiological signal from the sensor configuration. The mobile device may also include a qualitative module to conduct a qualitative analysis for each of a plurality of noise sources in the physiological signal to obtain a corresponding plurality of qualitative ratings, and a selection module to use at least the plurality of qualitative ratings to determine whether to report the physiological signal to a remote location.

Example 2 may include the mobile device of Example 1, further including a quantitative module to conduct a quantitative analysis for each of the plurality of noise sources to obtain an overall quality level, wherein the overall quality level is to be used to determine whether to report the physiological signal to the remote location.

Example 3 may include the mobile device of Example 2, wherein the quantitative module is to assign weights to signal to noise ratios associated with the plurality of noise sources based on the plurality of qualitative ratings.

Example 4 may include the mobile device of Example 1, wherein the qualitative module is to combine the plurality of qualitative ratings into an overall qualitative rating, and wherein the overall qualitative rating is to be used to determine whether to report the physiological signal to the remote location.

Example 5 may include the mobile device of Example 1, further including a user interface to generate a user prompt if a quality condition is not satisfied, wherein the user prompt is to request one or more additional readings and include a recommendation that is tailored to one or more of the plurality of noise sources.

Example 6 may include the mobile device of any one of Examples 1 to 5, further including a noise extraction module to filter, for each of the plurality of noise sources, the physiological signal, and a noise estimation module to conduct a noise estimation for the filtered physiological signal.

Example 7 may include an apparatus to evaluate physiological signals, comprising a sensor interface to receive a physiological signal from a sensor configuration associated with a mobile device, a qualitative module to conduct a qualitative analysis for each of a plurality of noise sources in the physiological signal to obtain a corresponding plurality of qualitative ratings, and a selection module to use at least the plurality of qualitative ratings to determine whether to report the physiological signal to a remote location.

Example 8 may include the apparatus of Example 7, further including a quantitative module to conduct a quantitative analysis for each of the plurality of noise sources to obtain an overall quality level, wherein the overall quality level is to be used to determine whether to report the physiological signal to the remote location.

Example 9 may include the apparatus of Example 8, wherein the quantitative module is to assign weights to signal to noise ratios associated with the plurality of noise sources based on the plurality of qualitative ratings.

Example 10 may include the apparatus of Example 7, wherein the qualitative module is to combine the plurality of qualitative ratings into an overall qualitative rating, and wherein the overall qualitative rating is to be used to determine whether to report the physiological signal to the remote location.

Example 11 may include the apparatus of Example 7, further including a user interface to generate a user prompt if a quality condition is not satisfied, wherein the user prompt is to request one or more additional readings and include a recommendation that is tailored to one or more of the plurality of noise sources.

Example 12 may include the apparatus of any one of Examples 7 to 11, further including a noise extraction module to filter, for each of the plurality of noise sources, the physiological signal, and a noise estimation module to conduct a noise estimation for the filtered physiological signal.

Example 13 may include a method of evaluating physiological signals, comprising receiving a physiological signal from a sensor configuration associated with a mobile device, conducting a qualitative analysis for each of a plurality of noise sources in the physiological signal to obtain a corresponding plurality of qualitative ratings, and using at least the plurality of qualitative ratings to determine whether to report the physiological signal to a remote location.

Example 14 may include the method of Example 13, further including conducting a quantitative analysis for each of the plurality of noise sources to obtain an overall quality level, wherein the overall quality level is used to determine whether to report the physiological signal to the remote location.

Example 15 may include the method of Example 14, further including assigning weights to signal to noise ratios associated with the plurality of noise sources based on plurality of qualitative ratings.

Example 16 may include the method of Example 13, further including combining the plurality of qualitative ratings into an overall qualitative rating, wherein the overall qualitative rating is used to determine whether to report the physiological signal to the remote location.

Example 17 may include the method of Example 13, further including generating a user prompt if a quality condition is not satisfied, wherein the user prompt requests or more additional readings and includes a recommendation that is tailored to one or more of the plurality of noise sources.

Example 18 may include the method of any one of Examples 13 to 17, further including filtering, for each of the plurality of noise sources, the physiological signal, and conducting a noise estimation for the filtered physiological signal.

Example 19 may include at least one computer readable storage medium comprising a set of instructions which, if executed by a mobile device, causes the mobile device to perform the method of any one of Examples 13 to 18.

Example 20 may include an apparatus to evaluate physiological signals, comprising means for performing the method of any one of Examples 13 to 18.

Thus, techniques described herein may therefore automatically assess physiological signal quality by measuring contributions due to multiple types of noise. Additionally, rather than relying on a single noise type, techniques may synthesize a holistic signal quality assessment. Moreover, since noise types may be separately extracted and quantified, it is also possible to point out the exact cause of the noise to the end user/patient. Such an approach may enable the patient to precisely correct the cause of the noise in successive measurements. In addition, a dynamic weighting approach may bias analysis results so that excessive contamination from a single noise source (which is typically unacceptable), over mild/moderate contamination from multiple noise sources (which may be acceptable). Techniques may also enhance performance by selecting the best quality metrics from a set of re-measurement results.

Accordingly, the likelihood of generating clinically acceptable physiological signals may be improved because only those physiological signals with clinically acceptable quality may be sent to the healthcare network for interpretation by a medical professional. Turnaround time for desired medical advice may also be significantly reduced under the techniques described herein. The techniques may also enable individuals with little or no medical or technical training to self-measure their own physiological condition in remote/home settings. Indeed, various risk-mitigation requirements associated with medical standards may be satisfied using the techniques described herein.

Embodiments of the present invention are applicable for use with all types of semiconductor integrated circuit ("IC") chips. Examples of these IC chips include but are not limited to processors, controllers, chipset components, programmable logic arrays (PLAs), memory chips, network chips, systems on chip (SoCs), SSD/NAND controller ASICs, and the like. In addition, in some of the drawings, signal conductor lines are represented with lines. Some may be different, to indicate more constituent signal paths, have a number label, to indicate a number of constituent signal paths, and/or have arrows at one or more ends, to indicate primary information flow direction. This, however, should not be construed in a limiting manner. Rather, such added detail may be used in connection with one or more exemplary embodiments to facilitate easier understanding of a circuit. Any represented signal lines, whether or not having additional information, may actually comprise one or more signals that may travel in multiple directions and may be implemented with any suitable type of signal scheme, e.g., digital or analog lines implemented with differential pairs, optical fiber lines, and/or single-ended lines.

Example sizes/models/values/ranges may have been given, although embodiments of the present invention are not limited to the same. As manufacturing techniques (e.g., photolithography) mature over time, it is expected that devices of smaller size could be manufactured. In addition, well known power/ground connections to IC chips and other components may or may not be shown within the figures, for simplicity of illustration and discussion, and so as not to obscure certain aspects of the embodiments of the invention. Further, arrangements may be shown in block diagram form in order to avoid obscuring embodiments of the invention, and also in view of the fact that specifics with respect to implementation of such block diagram arrangements are highly dependent upon the platform within which the embodiment is to be implemented, i.e., such specifics should be well within purview of one skilled in the art. Where specific details (e.g., circuits) are set forth in order to describe example embodiments of the invention, it should be apparent to one skilled in the art that embodiments of the invention can be practiced without, or with variation of, these specific details. The description is thus to be regarded as illustrative instead of limiting.

The term "coupled" may be used herein to refer to any type of relationship, direct or indirect, between the components in question, and may apply to electrical, mechanical, fluid, optical, electromagnetic, electromechanical or other connections. In addition, the terms "first", "second", etc. are used herein only to facilitate discussion, and carry no particular temporal or chronological significance unless otherwise indicated.

Those skilled in the art will appreciate from the foregoing description that the broad techniques of the embodiments of the present invention can be implemented in a variety of forms. Therefore, while the embodiments of this invention have been described in connection with particular examples thereof, the true scope of the embodiments of the invention should not be so limited since other modifications will become apparent to the skilled practitioner upon a study of the drawings, specification, and following claims.

I claim:

1. At least one storage device or storage disk comprising instructions that, when executed, cause at least one processor of a mobile electronic device to at least:
   determine an amount of noise associated with a first noise source in physiological signal data collected from a user via one or more human body sensors, the noise associated with the first noise source indicative of interference from a power line in an environment in which the user is located during collection of the physiological signal data;
   determine an amount of noise associated with a second noise source in the physiological signal data, the noise associated with the second noise source corresponding to a baseline noise associated with a coupling of the one or more human body sensors to skin of the user; and
   output one or more signals based on at least one of the amount of noise associated with the first noise source or the amount of noise associated with the second noise source.

2. The at least one storage device or storage disk as defined in claim 1, wherein the instructions, when executed, cause the at least one processor to determine a signal to noise ratio for at least one of the noise associated with the first noise source or the noise associated with the second noise source.

3. The at least one storage device or storage disk as defined in claim 2, wherein the instructions, when executed, cause the at least one processor to:
   determine a first signal to noise ratio for the noise associated with the first noise source and a second signal to noise ratio for the noise associated with the second noise source; and
   assign a rating to the physiological signal data based on the first signal to noise ratio and the second signal to noise ratio, the one or more signals to convey rating data.

4. The at least one storage device or storage disk as defined in claim 3, wherein the instructions, when executed, cause the at least one processor to apply a weight to the first signal to noise ratio based on the amount of noise associated with the first noise source relative to the amount of noise associated with the second noise source.

5. The at least one storage device or storage disk as defined in claim 3, wherein the physiological signal data is first physiological signal data and the instructions, when executed, cause the least one processor to select one of the first physiological signal data or second physiological signal data for transmission to a remote device based on the rating.

6. The at least one storage device or storage disk as defined in claim 1, wherein the instructions, when executed, cause the at least one processor to filter the physiological signal data to extract the noise associated with the first noise source.

7. The at least one storage device or storage disk as defined in claim 1, wherein the physiological signal data is indicative of electrical activity from a muscle of the user.

8. The at least one storage device or storage disk as defined in claim 1, wherein the one or more signals convey alert data.

9. The at least one storage device or storage disk as defined in claim 1, wherein the instructions, when executed, cause the at least one processor to cause a prompt to be output via the mobile electronic device based on at least one of the amount of noise associated with the first noise source or the amount of noise associated with the second noise source, the prompt to include a recommendation for collecting the physiological signal data.

10. An apparatus for monitoring physiological signal data, the apparatus comprising:
    a sensor interface configured to access physiological signal data collected from a user via one or more human body sensors; and
    a noise quantifier configured to:
       determine an amount of noise associated with a first noise source in the physiological signal data collected from the user via the one or more human body sensors, the first noise source associated with external electrical interference in an environment in which the user is located during collection of the physiological signal data;

determine an amount of noise associated with a second noise source in the physiological signal data, the second noise source corresponding to noise associated with contact between the one or more human body sensors and skin of the user that originates from changes in skin-electrode impedance; and output one or more signals based on at least one of the amount of noise associated with the first noise source or the amount of noise associated with the second noise source.

11. The apparatus as defined in claim 10, wherein the sensor interface is further configured to access the physiological signal data via wireless communication.

12. The apparatus as defined in claim 10, wherein the external electrical interference includes electromagnetic interference associated with one or more electrical devices in the environment.

13. The apparatus as defined in claim 10, further including a filter configured to extract one or more of the noise associated with the first noise source or the noise associated with the second noise source from the physiological signal data.

14. The apparatus as defined in claim 13, wherein the filter is further configured to block the first noise source in a frequency range from 50 Hz to 60 Hz.

15. The apparatus as defined in claim 10, wherein the physiological signal data is indicative of electrical activity from a muscle of the user.

16. The apparatus as defined in claim 10, wherein the noise quantifier is further configured to determine a signal to noise ratio for at least one of the noise associated with the first noise source or the noise associated with the second noise source.

17. The apparatus as defined in claim 10, wherein the noise associated with the second noise source is baseline wander noise.

18. An apparatus comprising:
means for obtaining physiological signal data from a user; and
means for evaluating the physiological signal data, the means for evaluating being configured to:
determine an amount of noise associated with a first noise source in the physiological signal data collected from the user by the means for obtaining, the first noise source associated with external electrical interference in an environment in which the user is located during collection of the physiological signal data;
determine an amount of noise associated with a second noise source in the physiological signal data, the second noise source corresponding to a baseline noise associated with a coupling between the means for obtaining and skin of the user; and
output one or more indicators based on at least one of the amount of noise associated with the first noise source or the amount of noise associated with the second noise source.

19. The apparatus as defined in claim 18, wherein the one or more indicators include an alert.

20. The apparatus as defined in claim 18, wherein the external electrical interference includes electromagnetic interference associated with one or more electrical devices in the environment.

21. The apparatus as defined in claim 18, wherein the physiological signal data is indicative of electrical activity from a muscle of the user.

22. The apparatus as defined in claim 18, further including circuitry configured to filter the physiological signal data to extract one or more of the noise associated with the first noise source or the noise associated with the second noise source.

23. The apparatus as defined in claim 18, wherein the means for evaluating is further configured to determine a signal to noise ratio for at least one of the noise associated with the first noise source or the noise associated with the second noise source.

\* \* \* \* \*